(12) United States Patent
Kang et al.

(10) Patent No.: US 10,179,934 B2
(45) Date of Patent: Jan. 15, 2019

(54) HIGH-THROUGHPUT DETECTION METHOD FOR DNA SYNTHESIS PRODUCT

(71) Applicant: BGI Shenzhen, Shenzhen, Guangdong (CN)

(72) Inventors: Kang Kang, Guangdong (CN); Shihong Chen, Guangdong (CN); Yue Shen, Guangdong (CN); Yun Wang, Guangdong (CN); Xun Xu, Guangdong (CN)

(73) Assignee: BGI Shenzhen, Shenzhen, Guangdong (CN)

( * ) Notice: Subject to any disclaimer, the term of this patent is extended or adjusted under 35 U.S.C. 154(b) by 0 days.

(21) Appl. No.: 15/643,078

(22) Filed: Jul. 6, 2017

(65) Prior Publication Data

US 2017/0349945 A1    Dec. 7, 2017

Related U.S. Application Data

(63) Continuation of application No. PCT/CN2015/070459, filed on Jan. 9, 2015.

(51) Int. Cl.

| | | |
|---|---|---|
| *C12Q 1/68* | (2018.01) | |
| *C12Q 1/6876* | (2018.01) | |
| *C12Q 1/6874* | (2018.01) | |
| *C12Q 1/6806* | (2018.01) | |
| *C12N 15/00* | (2006.01) | |

(52) U.S. Cl.
CPC .......... *C12Q 1/6876* (2013.01); *C12N 15/00* (2013.01); *C12Q 1/6806* (2013.01); *C12Q 1/6874* (2013.01)

(58) Field of Classification Search
None
See application file for complete search history.

(56) References Cited

FOREIGN PATENT DOCUMENTS

| | | |
|---|---|---|
| CN | 1251615 A | 4/2000 |
| WO | 2014018512 A1 | 1/2014 |

OTHER PUBLICATIONS

Int'l Search Report dated Nov. 6, 2015 in Int'l Application No. PCT/CN2015/070459.
Eroshenko et al., "Gene Assembly from Chip-Synthesized Oligonucleotides", Curr Protoc Chem Biol., 24 pgs. (2012).
Nirenberg et al., "The Dependence of Cell-Free Protein Synthesis in *E.coli* Upon Naturally Occurring or Synthetic Polyribonucleotides", Proc. Natl. Acad. Sci., vol. 47, pp. 1588-1602 (1961).
Gibson et al., "Creation of a Bacterial Cell Controlled by a Chemically Synthesized Genome", Science, vol. 329, pp. 52-56 (Jul. 2, 2010).
Gibson, "Synthesis of DNA Fragments in Yeast by One-Step Assembly of Overlapping Oligonucleotides", Nucleic Acids Research, vol. 37, No. 20, pp. 6984-6990 (2009).
Li et al., "Harnessing Homologous Recombination in vitro to Generate Recombinant DNA via SLIC", Nature Methods, vol. 4, No. 3, pp. 251-256 (Mar. 2007).
Bang et al., "Gene Synthesis by Circular Assembly Amplification" Nature Methods, vol. 5, No. 1, pp. 37-39 (Jan. 2008).
Shao et al., "DNA Assembler, an in vivo Genetic Method for Rapid Construction of Biochemical Pathways", Nucleic Acids Research, vol. 37, No. 2, 10 pgs (2009).
Tian et al., "Accurate Multiplex Gene Synthesis from Programmable DNA Microchips", Nature, vol. 432, pp. 1050-1054 (Dec. 2004).
Kosuri et al., "Scalable Gene Synthesis by Selective Amplification of DNA Pool from High-Fidelity Microchips", Nature Bio., vol. 28, No. 12, pp. 1295-1299 (Dec. 2010).

*Primary Examiner* — James S Ketter
(74) *Attorney, Agent, or Firm* — Panitch Schwarze Belisario & Nadel LLP

(57) ABSTRACT

Disclosed is a high-throughput detection method for a DNA synthesis product. According to the method of the present invention, a high-throughput sequencing technology is applied to detection of a DNA chip synthesis product through a mixed library construction strategy, so that costs of product detection and accurate product screening are reduced.

17 Claims, 1 Drawing Sheet

Specification includes a Sequence Listing.

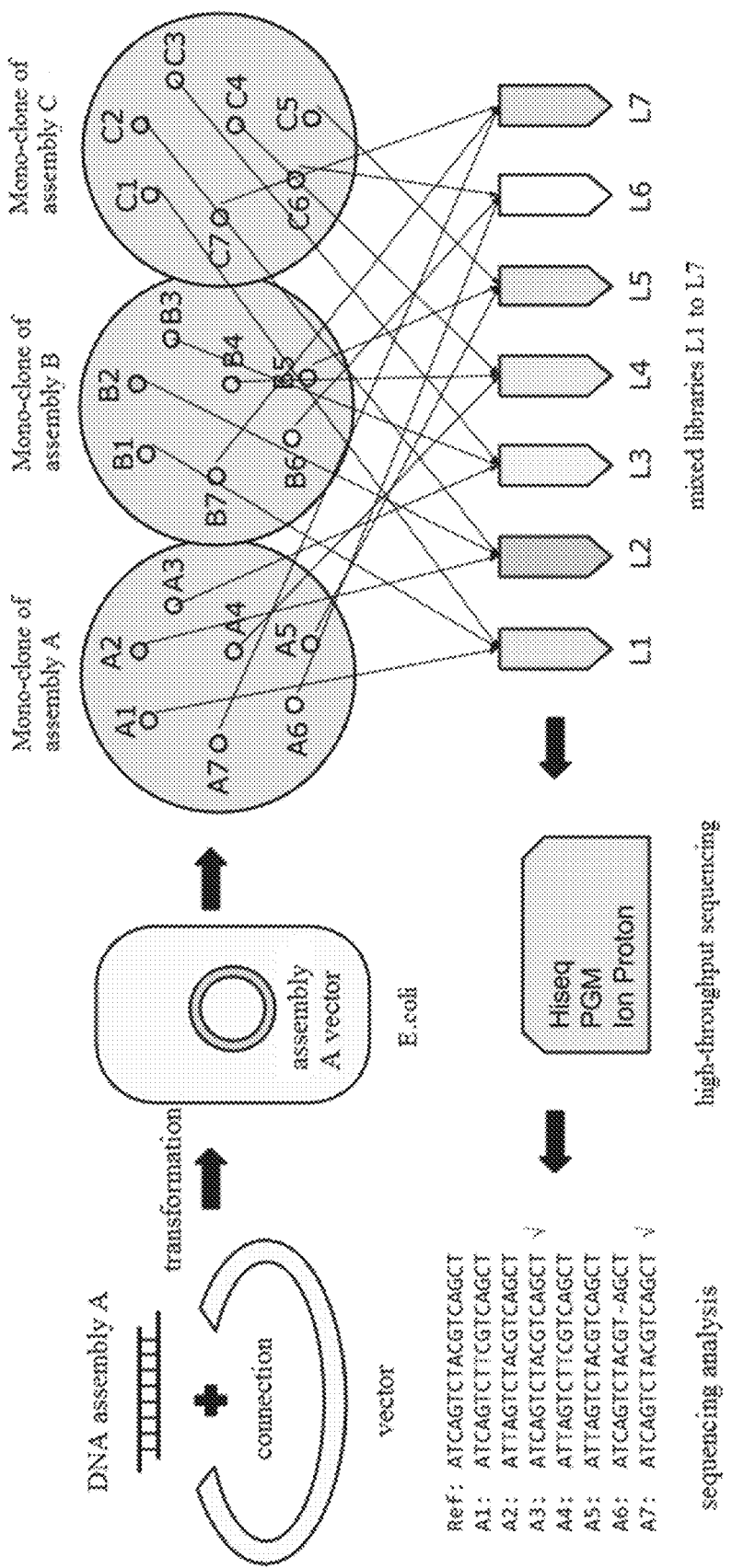

SEQUENCE LISTING

<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: Ref sequence of Figure 1

<400> SEQUENCE: 1
atcagtctac gtcagct         17

<210> SEQ ID NO 2
<211> LENGTH: 17
<212> TYPE: DNA
<213> ORGANISM: Artificial Sequence
<220> FEATURE:
<223> OTHER INFORMATION: Sequence A1 of Figure 1

<400> SEQUENCE: 2
atcagtcttc gtcagct         17

<210> SEQ ID NO 3
<211> LENGTH: 17
<212> TYPE: DNA
<213> ORGANISM: Artificial Sequence
<220> FEATURE:
<223> OTHER INFORMATION: Sequence A2 of Figure 1

<400> SEQUENCE: 3
attagtctac gtcagct         17

<210> SEQ ID NO 4

```
<211> LENGTH: 17
<212> TYPE: DNA
<213> ORGANISM: Artificial Sequence
<220> FEATURE:
<223> OTHER INFORMATION: Sequence A3 of Figure 1

<400> SEQUENCE: 4
atcagtctac gtcagct                                                  17

<210> SEQ ID NO 5
<211> LENGTH: 17
<212> TYPE: DNA
<213> ORGANISM: Artificial Sequence
<220> FEATURE:
<223> OTHER INFORMATION: Sequence A4 of Figure 1

<400> SEQUENCE: 5
attagtcttc gtcagct                                                  17

<210> SEQ ID NO 6
<211> LENGTH: 17
<212> TYPE: DNA
<213> ORGANISM: Artificial Sequence
<220> FEATURE:
<223> OTHER INFORMATION: Sequence A5 of Figure 1

<400> SEQUENCE: 6
attagtctac gtcagct                                                  17

<210> SEQ ID NO 7
<211> LENGTH: 16
<212> TYPE: DNA
<213> ORGANISM: Artificial Sequence
<220> FEATURE:
<223> OTHER INFORMATION: Sequence A6 of Figure 1

<400> SEQUENCE: 7
atcagtctac gtagct                                                   16

<210> SEQ ID NO 8
<211> LENGTH: 17
<212> TYPE: DNA
<213> ORGANISM: Artificial Sequence
<220> FEATURE:
<223> OTHER INFORMATION: Sequence A7 of Figure 1

<400> SEQUENCE: 8
atcagtctac gtcagct                                                  17
```

HIGH-THROUGHPUT DETECTION METHOD FOR DNA SYNTHESIS PRODUCT

CROSS-REFERENCE TO RELATED APPLICATION

This application is a continuation of International Application No. PCT/CN2015/070459, filed Jan. 9, 2015, which was published in the Chinese language on Jul. 14, 2016, under International Publication No. WO/2016/109981, and the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688806.13 Sequence Listing" and a creation date of Aug. 22, 2017, and having a size of 1.9 KB. The sequence listing submitted via EFS-Web is part of the specification and is herein incorporated by reference in its entirety.

FIELD OF THE INVENTION

The present invention relates to the technical field of DNA synthesis, in particular to a high-throughput detection method for DNA synthesis products.

BACKGROUND OF THE INVENTION

With the development of genetic science and genetic engineering, DNA synthesis technology plays an increasingly important role in the life sciences. The de novo synthesis of DNA assemblies, including the synthesis of regulatory sequences, whole genes, artificial metabolic pathways or even complete artificial genomes, will bring great changes to human life science research. Since the first oligonucleotide chain synthesis by a human in 1961 (Nirenberg et al. (1961) Proc. Natl. Acad. Sci. USA 54: 1588), DNA synthesis and assembly technologies have made great progress. At present, the synthesis and assembly of large DNA fragments are performed by way of assembling a number of oligonucleotide fragments below 100 bp due to certain technical limitations (Gibson, et al. (2010) Science 329: 52; Gibson. (2009) Nucleic. Acids Res. 37: 6984; Li & Elledge (2007) Nat. Methods 4: 251; Bang & Church (2008) Nat. Methods 5: 37; Shao et al. (2009) Nucleic Acids Res. 37: e16), and the associated cost is roughly stabilized at about 2.2 yuan per base pair (bp). Thus, traditional DNA synthesis and assembly methods, due to cost limitations, are difficult to apply to genomic DNA synthesis.

In 2004, using oligonucleotide microarray chips, Tian Jingdong et al. successfully synthesized 292 different oligonucleotide fragments on DNA chips, which were then assembled into a 14.6-kb DNA fragment. The foregoing work makes it feasible to perform chip-based large-scale DNA long-fragment synthesis and assembly with high efficiency and low cost (Tian (2004) Nature 432: 1050). In 2010, Kosuri et al. utilized Agilent's commercial DNA microarray chips to achieve the synthesis of hundreds of genes (Kosuri et al. (2010) Nat. Biotech. 28: 1295) and provide a complete and established technical route (Eroshenko et al. (2012) Curr. Protoc. in Chem. Biol. 4: 1). Based on this technology, the GEN9 Company was founded in the United States in 2012 and became the first commercial company to offer on-chip DNA synthesis services around the world. The price of its DNA synthesis products is about USD 0.26 per bp, which is lower than the market price of traditional DNA synthesis.

On-chip DNA synthesis technology is currently facing two major challenges, which are high error rates of the oligonucleotide chains, and the impact from the oligonucleotide library's high complexity on the assembly. Hence, further improvement on the accuracy rate of on-chip DNA synthesis technology and reduction in the cost for assembly and screening will play a crucial role in commercial applications of the on-chip DNA synthesis technology. In the technical route of the existing on-chip DNA synthesis technology, measurement of the accuracy rate of synthesis of DNA fragments and screening for accurate fragments are typically accomplished by way of first-generation sequencing technology, the Sanger sequencing process. Due to the technical bottlenecks of the technology of on-chip DNA synthesis, assembly products tend to be more complex when compared with the original designed sequence, that is to say the assembled DNA molecule can have multiple variations with high complexity in its sequence (including single base variation, nucleotide insertion and deletion, etc.), wherein the probability of single base variation is about 0.1% to 1% depending on the differences of platform and design. As a result, in the case that the single base error rate is 0.5%, when assembling a DNA fragment of 750 bp, the probability of obtaining a completely accurate DNA fragment in one synthesis is only 2.33%, the probability of having no more than one base error is 11.11%, and the probability of having no more than two base errors is 27.63%. As a result, in order to find an accurate molecule whose sequence is completely consistent with the designed sequence from the complex DNA assembly products and ensure a success rate of 90%, at least 98 monoclones have to be selected for Sanger sequencing. In the foregoing case, if the cost for each Sanger reaction is 20 yuan, the total cost for the foregoing process would be about 1,960 yuan, which is equal to 2.61 yuan per bp and is significantly higher than that of the traditional synthesis method. Moreover, in order to find at least one clone with no more than one base error and meanwhile ensure a success rate of 90%, 20 monoclones have to be selected for Sanger sequencing verification. In this case, the cost for such verification is about 400 yuan, which is equal to 0.53 yuan per bp. Further, in order to find at least one clone with no more than two base errors and meanwhile ensure a success rate of 90%, 8 monoclones have to be selected for Sanger sequencing verification. In this case, the cost for such verification is about 160 yuan, which is equal to 0.21 yuan per bp. However, when the clones selected have more than 3 base errors, the associated cost for material and time in the process of error removal would be considerably high. Accordingly, the on-chip DNA synthesis technology will lose its cost advantages. In light of the foregoing, it can be seen that the traditional method for measuring the accuracy rate of DNA chip synthesis products based on Sanger sequencing has a relatively high cost, which is the main source of the cost associated with the on-chip DNA synthesis technology, as well as one of the major bottlenecks of this technology to further reduce the cost.

SUMMARY OF THE INVENTION

The present invention provides a high-throughput detection method for DNA synthesis products. The method successfully utilizes high-throughput sequencing technology to detect the DNA chip synthesis product through the strategy of constructing mixed libraries, which enables great reduction in the costs for product detection and accurate product screening, so as to significantly reduce the cost of on-chip DNA synthesis.

The present invention is achieved by way of the following technical solution:

A high-throughput detection method for DNA synthesis products, characterized in that the method comprises the following steps:

1) respectively connecting a plurality of DNA assemblies produced by the synthesis into cloning vectors, which are then respectively transformed into screening bacterial strains, which are respectively cultured on a selection culture medium, so as to enable screening for clones containing the DNA assemblies;

2) sequentially numbering the clones of each of the DNA assemblies;

3) selecting clones assigned the same number but having different DNA assemblies, culturing them in a mixture to obtain a corresponding mixed bacterial solution, and then extracting their plasmids to obtain a mixed plasmid sample; alternatively, culturing the clones of each one of the DNA assemblies, respectively, to obtain corresponding bacterial solutions, selecting and mixing the bacterial solutions of the clones assigned the same number but having different DNA assemblies, and extracting their plasmids to obtain a mixed plasmid sample;

4) attaching sequencing indexes to a plurality of the mixed plasmid samples to construct a plurality of mixed sequencing libraries, wherein the sequencing indexes for different mixed sequencing libraries are different;

5) carrying out a high-throughput mixed sample sequencing process with the plurality of mixed sequencing libraries, so as to obtain sequences of DNA assemblies carried in selected clones;

6) comparing the sequences of the DNA assemblies obtained in the foregoing sequencing process to reference sequences, so as to obtain target DNA assemblies having a preset accuracy rate in the DNA synthesis products.

As a preferred technical solution of the present invention, the DNA synthesis products are DNA assemblies synthesized and assembled with a DNA chip.

As a preferred technical solution of the present invention, the method further comprises a step between step 1) and step 2): picking selected clones for colony PCR confirmation, so as to further screen for clones having an inserted fragment size consistent with the size of the corresponding DNA assembly.

As a preferred technical solution of the present invention, in step 3), the process of mixing clone bacterial solutions is carried out in accordance with the principle of each clone having the same amount of bacteria;

and preferably, preserving the bacterial solution obtained from culturing the clone of each one of the DNA assemblies for future use.

As a preferred technical solution of the present invention, step 4) specifically comprises: respectively obtaining or amplifying mixed DNA assemblies from the mixed plasmid samples, and attaching sequencing indexes to a plurality of the mixed DNA assemblies to construct a plurality of mixed sequencing libraries, wherein the sequencing indexes for different mixed sequencing libraries are different;

and preferably, further comprises: after attaching the sequencing indexes, attaching sequencing adaptors to a plurality of the mixed DNA assemblies.

As a preferred technical solution of the present invention, in step 4), the mixed DNA assemblies are obtained or amplified from the mixed plasmids sample by way of enzymatic digestion or PCR.

As a preferred technical solution of the present invention, in step 5), one of the following sequencing devices or single-molecule sequencing devices is utilized in the high-throughput sequencing process: Illumina HiSeq2000, HiSeq2500, MiSeq, MiSeqDx, NextSeq500, Hiseq X ten, Life SOLiD, Ion Torrent PGM, Proton, Roche 454, and Complete Genomics.

As a preferred technical solution of the present invention, the preset accuracy rate mentioned herein refers to a base accuracy rate of 100%.

As a preferred technical solution of the present invention, the method further comprises: in the case when the preset accuracy rate is lower than 100%, carrying out an error removal process through a single point mutation;

preferably, in the case when the preset accuracy rate is lower than 100%, selecting the clones having the lowest single point mutation or mutation of insertion or deletion for error removal process through the single point mutation;

preferably, further comprises confirming a product of the error removal process by way of a Sanger sequencing process.

As a preferred technical solution of the present invention, the target DNA assemblies are verified by way of a Sanger sequencing process.

As a preferred technical solution of the present invention, the method further comprises: in the case when a DNA assembly fails to reach the preset accuracy rate, repeating steps 2) to 6) for the DNA assembly to screen the clones that have not yet been selected, constructing the mixed sequencing libraries and then carrying out sequencing, or repeating steps 4) to 6) for the mixed plasmid samples that have not yet been sequenced, constructing the mixed sequencing libraries and then carrying out sequencing.

As a preferred technical solution of the present invention, the method further comprises a step after step 6): finding a clone and/or a clone bacterial solution corresponding to the target DNA assembly having the preset accuracy rate, and then extracting the plasmid and/or carrying out an amplification process for the DNA assembly.

The method of the present invention successfully utilizes the high-throughput sequencing technology to detect the DNA chip synthesis product through the strategy of constructing mixed libraries and high-throughput sequencing with a mixed sample, which takes advantage of the low cost of the high-throughput sequencing technology to greatly reduce the costs for synthesis product detection and accurate product screening. Upon calculation, it has been found that the cost for sequencing detection of the DNA assembly synthesis products can be reduced by about two orders, thereby greatly reducing the cost of on-chip DNA synthesis.

BRIEF DESCRIPTION OF THE DRAWINGS

FIG. 1 is a schematic flow chart showing the process of using a high-throughput sequencing strategy to detect the products of on-chip DNA synthesis according to the present invention, wherein Ref is SEQ ID NO: 1, A1 is SEQ ED NO: 2, A2 is SEQ ID NO: 3, A3 is SEQ ID NO: 4, A4 is SEQ ID NO: 5, A5 is SEQ ID NO: 6, A6 is SEQ ID NO: 7, and A7 is SEQ ID NO: 8.

DETAILED DESCRIPTION OF THE INVENTION

The present invention will now be described in further detail by way of describing specific examples. Unless otherwise specified, the techniques used in the examples below are conventional techniques known to one of ordinary skill in the art; the instruments and reagents used herein can be obtained by one of ordinary skill in the art through common routes such as commercial purchase.

The terms used in the present invention are as follows:

DNA Assembly refers to a double-stranded DNA fragment product produced by a DNA synthesis technology (including but not limited to the on-chip DNA synthesis technology). Its length is typically within the range of from 400 bp to 1.5 kbp.

Target DNA assembly refers to a double-stranded DNA fragment product produced by a DNA synthesis technology in which the base accuracy rate thereof detected by the method according to the present invention reaches a preset accuracy rate (e.g., base accuracy rate of 100%).

Mixed Sequencing Library or Mixed Library refers to a mixed DNA sequencing library derived from different DNA assemblies, wherein each DNA assembly contains only a single type of DNA molecule, such as plasmid molecules, PCR amplification products or enzymatic digestion products derived from a monoclone.

In reference to FIG. 1, in one embodiment of the present invention, the high-throughput detection method for DNA synthesis products generally comprises the following process:

(1) A plurality (a plurality refers to more than two, for example, a total of 400) of DNA assemblies produced by a DNA chip are ligated into a vector by way of enzyme digestion and ligation, Gibson assembly, or T vector connection, which are then transformed into a screening strain such as E. coli, and cultured on a culture plate with a correspondingly resistance to grow a sufficient number (for example, 30) of clearly identifiable monoclones. Depending on the specific need, the vectors with blue-white plaque screening or other screening function can be used to reduce the false positive clonal rate.

(2) As an optional step, a sufficient number of monoclones are picked. The colonies thereof are then subjected to PCR verification using primers corresponding to the vector or specifically designed primers (such as primers based on the sequences contained within the DNA assembly) and screened for the clones whose insert fragment size is consistent with the size of the designed assembly. By way of the colony PCR verification, the rate of false positive clones can be further reduced, so as to ensure that all of the clones used in the construction of the mixed sequencing library contain an insert fragment of target length. In this way, the step of sequencing for unnecessary false positive clones is spared, which helps to improve the sequencing efficiency.

(3) The clones of each DNA assembly are sequentially numbered (for example, for assembly A, the clones can be sequentially numbered from #1 to #30; for assembly B, the clones can be sequentially numbered from #1 to #20), the monoclones are further cultured and expanded on a 96-well culture plate or in a culture tube to obtain a corresponding expanded bacterial solution, and the bacteria are preserved using a deep-hole plate, centrifuge tube or culture plate.

(4) The expanded bacterial solutions assigned the same number and derived from different DNA assemblies are mixed in equal bacterial amount (before mixing, the concentration of bacteria in each bacterial solution can be estimated or determined by measuring an OD value of the bacterial solution to ensure that roughly equal or close amounts of different bacteria are added to the mixture), and then the mixed plasmid DNA are extracted from bacterial solutions, and the extracted mixed plasmid DNA samples are numbered according to the corresponding clone numbers (such as DNA #1 to DNA #30).

(5) As an optional step, the DNA molecules of the mixed DNA assemblies are obtained or amplified from the mixed plasmid DNA samples by way of enzymatic digestion or PCR amplification or the like. This step is an optional step because the methods of constructing the sequencing library can be very different for different high-throughput sequencing platforms. For some sequencing libraries, they can be constructed by directly linking the linear plasmid DNA to a specific sequencing index and sequencing adaptor to generate the sequencing libraries for machine sequencing; while for other sequencing libraries, they may require use of a DNA assembly as the starting molecule, and at the two ends of the starting molecule, specific sequencing indexes and sequencing connecters are further added to construct a corresponding sequencing library.

(6) A certain amount of mixed plasmid DNA or mixed DNA assemblies are selected according to the requirements of respective high-throughput sequencing platforms (for example, Hiseq, Miseq, PGM, Proton, CG, PacBio, and the like), which are then linked with various sequencing indexes and/or sequencing adaptors to construct a plurality of mixed sequencing libraries (for example, L #1 to L #10). In this context, the sequencing indexes are used to distinguish the DNA assemblies derived from different sources, i.e., to distinguish the DNA assemblies from different mixed sequencing libraries. Each sequencing library has a sequencing index having a specific sequence, and the specific sequences of the sequencing indexes for different sequencing libraries are different from each other. Typically, a sequencing index can be a sequence containing a few or a dozen of bases, which can be a random sequence, such as a random sequence of 8 to 12 bases, and the like. A sequencing adaptor is a linking sequence specific to a high-throughput sequencing platform; different high-throughput sequencing platforms have different sequencing adaptors.

(7) A certain amount of the samples of the foregoing generated mixed sequencing libraries are mixed and loaded into a machine for high-throughput sequencing. The amount of sequencing data is relatively low. To ensure that DNA assembly of each monoclone has a sequencing depth of 100×, each DNA assembly is 750 bp in length, about 400 different DNA assemblies are mixed in a mixed sequencing library, and 10 mixed sequencing libraries are sequenced at the same time, and the amount of sequencing data is only 300 Mbp; while in the case that the sequencing molecules are the vectors containing the respective DNA assemblies rather than the PCR products or enzymatic digestion products of the respective DNA assemblies, the amount of sequencing data is 1.1 Gbp.

(8) The sequencing data generated by the sequencing machine is next analyzed by certain bioinformatics approaches (for example, BWA comparison and GATK analysis); on the basis of respective sequencing library numbers, the DNA assembly sequence accuracy information of each monoclone is obtained.

(9) For the clones with a completely accurate sequence or with the sequence of highest accuracy, the bacterial solution preserved in step (3) is used for further plasmid DNA extraction and/or amplification, and the obtained plasmid DNA is used in subsequent experiments. According to certain specific needs, a specific accuracy rate can be preset for base accuracy, for example, the base error does not exceed 3, 2 or 1, or the base accuracy rate of 100%, and so on. If the sequenced DNA assembly has a certain base error, the error in the sequence can be removed by way of single point mutation using specifically designed mutagenesis primers.

(10) As an optional step, the sequence accuracy of the selected clones with a completely accurate sequence or the clones with the sequence of highest accuracy that have been subjected to an error removal process is further confirmed using the Sanger sequencing approach.

(11) In the case that among the selected clones, the accuracy rate of some DNA assemblies is still undesirable, for those DNA assemblies with the undesirable accuracy rate, the clones thereof that have not been sequenced can be further selected from step (3) for carrying out the construction of new mixed sequencing libraries; alternatively, the mixed plasmid DNA or mixed DNA assemblies thereof that have not been sequenced can be further selected from step (6) for carrying out the construction of new mixed sequencing libraries (for examples, L #11 to L #20); and the newly generated mixed sequencing libraries can be subjected a new round of sequencing confirmation. The foregoing procedures can be repeated until the clones with a desirable accuracy rate are obtained.

When compared with the existing method based on Sanger sequencing technology currently available in the art, the technical solution of the present invention based on high-throughput detection on the accuracy of DNA chip synthesis products and implementation of screening for the accurate fragments has the following advantages:

Using the 12 k chips provided by CustomArray as an example, each chip can synthesize about 400 different types of DNA assemblies, each DNA assembly has a length of 750 bases, the total synthesis length is 300,000 bases, and the rate of single base error is 0.5%. In this case, when assembling a DNA fragment of 750 bp, the probability of obtaining a completely accurate DNA fragment on one process is $0.995^{750}=2.33\%$. In addition, the probability of occurrence of no more than one base error is $0.995^{750}+750*0.005*0.995^{749}=11.11\%$; the probability of occurrence of no more than two base errors is $0.995^{750}+0.005*0.995^{749}+0.0052*0.995^{748}=27.63\%$. On the other hand, in order to select the accurate molecules with the sequence completely consistent with the corresponding designed sequence from the complex DNA assembling products and at the same time, ensure a 90% success rate, n, which is the number of the selected monoclones, shall satisfy the following conditions: $1-(1-2.33\%)^n>0.9$, and n is at least 98. Similarly, in order to select the at least one clone with no more than one base error and at the same time, ensure a 90% success rate, n, the number of the selected monoclones, shall satisfy the following conditions: $1-(1-11.11\%)^n>0.9$, n is at least 20; similarly, in order to select the at least one clone with no more than two base errors and at the same time, ensure a 90% success rate, n, the number of the selected monoclones, shall satisfy the following conditions: $1-(1-27.63\%)^n>0.9$, n is at least 8.

The cost of the existing technology based on Sanger sequencing technology and the cost of the present invention based on high-throughput sequencing technology are next compared as follows:

1. The existing technology based on Sanger sequencing technology 1.1 In the case when the probability of obtaining a completely accurate DNA assembly is higher than 90%:

| | |
|---|---|
| The probability of obtaining a fragment meeting the requirement in one process: | 2.33% |
| The number of clones needed to be screened for each DNA assembly: | 98 |
| The cost for sequencing 400 DNA assemblies: | 784,000 yuan |
| The average cost for a single base: | 2.61 yuan |

1.2 In the case when the probability of obtaining a DNA assembly with no more than one base error is higher than 90%:

| | |
|---|---|
| The probability of obtaining a fragment meeting requirement in one process: | 11.11% |
| The number of clones needed to be screened for each DNA assembly: | 20 |
| The cost for sequencing 400 DNA assemblies: | 160,000 yuan |
| The average cost for a single base: | 0.53 yuan |

1.3 In the case when the probability of obtaining a DNA assembly with no more than two base errors is higher than 90%:

| | |
|---|---|
| The probability of obtaining a fragment meeting the requirement in one process: | 27.63%, |
| The number of clones needed to be screened for each DNA assembly: | 8 |
| The cost for sequencing 400 DNA assemblies: | 64,000 yuan |
| The average cost for a single base: | 0.21 yuan |

2. The technical solution of the present invention based on high-throughput sequencing technology 2.1 In the case when the probability of obtaining a completely accurate DNA assembly is higher than 90%:

| | |
|---|---|
| The probability of obtaining a fragment meeting the requirement in one process: | 2.33% |
| The number of clones (number of libraries) needed to be screened for each DNA assembly: | 98 |
| The cost for constructing libraries for high-throughput sequencing | 21,560 yuan |
| The data needed for high-throughput sequencing | 10.78 G |
| The cost for obtaining the data for high-throughput sequencing | 5,390 yuan |
| The cost for sequencing 400 DNA assemblies: | 26,950 yuan |
| The average cost for a single base: | 0.090 yuan |
| The cost relative to the existing solution based on Sanger sequencing | 3.45% |

2.2 In the case when the probability of obtaining a DNA assembly with no more than one base error is higher than 90%:

| | |
|---|---|
| The probability of obtaining a fragment meeting the requirement in one process: | 11.11% |
| The number of clones (number of libraries) needed to be screened for each DNA assembly: | 20 |
| The cost for constructing libraries for high-throughput sequencing | 4,400 yuan |
| The data needed for high-throughput sequencing | 2.2 G |
| The cost for obtaining the data for high-throughput sequencing | 1,110 yuan |
| The cost for sequencing 400 DNA assemblies: | 5,500 yuan |
| The average cost for a single base: | 0.018 yuan |
| The cost relative to the existing solution based on Sanger sequencing | 3.40% |

2.3 In the case when the probability of obtaining a DNA assembly with no more than two base errors is higher than 90%:

| | |
|---|---|
| The probability of obtaining a fragment meeting the requirement in one process: | 27.63% |
| The number of clones (number of libraries) needed to be screened for each DNA assembly: | 8 |
| The cost for constructing libraries for high-throughput sequencing | 1,760 yuan |
| The data needed for high-throughput sequencing | 0.88 G |
| The cost for obtaining the data for high-throughput sequencing | 1,000 yuan |
| The cost for sequencing 400 DNA assemblies: | 2,760 yuan |
| The average cost for a single base: | 0.009 yuan |
| The cost relative to the existing solution based on Sanger sequencing | 4.30% |

It can be seen from the above comparison that the technical solution of the present invention based on high-throughput sequencing detection on DNA chip synthesis products can reduce the sequencing cost for detecting DNA assembly synthesis products by about two orders. Hence, a successful utilization of the method provided in the present invention can reduce the cost of single base by 0.2 to 0.5 yuan for industrialized on-chip DNA synthesis.

Example 1

In order to verify the effectiveness of the method provided in the present invention, 49 successfully assembled DNA assemblies of artificial chromosome 2 in artificial yeast genome were used for verification. All DNA assemblies were artificially designed yeast genomic fragments, and their lengths were within the range of from 450 to 650 bp. Ten clones were selected for each assembly, which were used to construct 10 mixed libraries. In addition, PGM sequencing was used in the verification.

The experimental process was as follows:

1. Acquisition of the assembled PCR products of DNA assembly:

In accordance with the manufacturer's instruction, CustomArray B3 synthesizer was used to synthesize and assemble the DNA assembly synthesis products of artificial chromosome 2 I1 to I6 regions (purified PCR product).

2. DNA assembly synthesis products were ligated to pMD18-T vector:

In accordance with the well-known method for the ligation of pMD18-T vector, Ex Taq enzyme was used to amplify the DNA assemblies and add a single base "A" to the 3' end thereof, and the amplification product was then ligated with the pMD18-T vector.

3. Vector transformation:

In accordance with the well-known method for *E. coli* DH5a transformation, the recombinant vector (pMD18-T vector ligation product) was transformed into *E. coli* DH5a cells, so as to clone the respective DNA assemblies.

4. Identification of monoclones:

After completion of the transformation, the transformation products were spread on plates for blue-white plaque screening. 5 μL of 20% IPTG and 40 μL of X-gal was added to each plate, which were then cultured overnight in an incubator at 37° C. When the plaques could be observed, white monoclones were selected.

5. Expansion and preservation of monoclones:

A suitable amount of white monoclones were picked from each plate (in this example, 10 clones were picked from each plate), which are then sequentially numbered (1, 2, 3, 4 . . . 10) and further cultured overnight under the condition of 37° C. and 200 rpm (to the platform stage); the obtained bacterial strains were then preserved.

6. Extraction of mixed plasmid DNA

The monoclones from each DNA assembly with the corresponding number were taken in a volume of 150 μL and mixed in a 15-mL centrifuge tube to form a sample library. Ten clones were picked for each DNA assembly; accordingly, 10 sample libraries were been generated.

Next, the plasmids were extracted from each sample library using a suitable plasmid extraction kit; the plasmids were then used to construct a corresponding mixed plasmid sample library. The mixed plasmid sample library was then used directly in the subsequent library generation and sequencing processes.

7. Construction and sequencing of high-throughput DNA sequencing library:

Ten sets of mixed plasmid samples were sent to the sequencing production platform (PGM400) at BGI Shenzhen. In accordance with well-known operating instructions, 10 sets of mixed sequencing libraries containing the specific sequencing indexes and sequencing adaptors needed for the PGM400 platform were generated, wherein different mixed sequencing libraries had different sequencing indexes. Next, the samples from the 10 sets of mixed sequencing libraries were mixed for PGM400 high-throughput sequencing, so as to obtain the sequence information of each DNA assembly.

8. Analysis of sequencing results 8.1 Construction of reference sequences:

The respective design sequences of the 49 DNA assemblies were obtained, the flanking regions of each DNA assembly were combined with 200 bp of the sequences flanking the insertion sites of pMD18-T vector, and the generated respective sequences, including the DNA assemblies combined with the flanking sequences, were saved as 49 reference sequences in FASTA format. Next, the bowtie2 (bowtie-bio.sourceforge.net/bowtie2) and picard (broadinstitute.github.io/picard) tools were used for index construction for the reference sequences.

8.2 Data filtering

The sequencing data were filtered with the respective parameters using the Filter_ion_bam.pl (provided by BGI Shenzhen):

-minlen 30-lowPhred 10-lowRate 0.01-Ns 0-trim-seed 20

In more detail, the parameters used are as follows: the shortest read length is 30 bp; the threshold for the low quality base for each read is 10; the threshold for the ratio of low quality bases among the reads is 0.01; the threshold for tolerating N number of ambiguous bases among the reads is 0; allowing deletion of the low quality bases at both ends of the reads, the length of the seed sequence is 20.

8.3 Alignment

Sequence alignment was further performed using bowtie2 with the following parameters:

-N 1--mp 10-R 3-D20-iS, 1,0.50.

In more detail, the parameters used are as follows: one mismatch is allowed when aligning the seed sequences; the penalty for mismatch is set to be 10; for a seed sequence with repeated appearance, the sequence can be repeatedly grown into a seed sequence 3 times; the number of extension attempts is 20; the distance between the seed sequences is set to be half of the square root of the length of the read plus 1. For alignment results having DNA assembly sequence alignment coverage less than 98%, the corresponding sample was discarded.

8.4 bam file sorting and library construction

The sorting function of samtools (www.htslib.org) was used to sort the generated bam files, and the alignment sequence index was constructed with samtools index.

8.5 Alignment with reference sequences

GATK (www.broadinstitute.org/gatk) was used for mutation detection and filtering. The RealignerTargetCreator tool in the GATK software was used for reference sequence revision for the regions close to insertion and deletion fragments.

8.6 Re-alignment

The IndelRealigner tool in the GATK software was used to perform re-alignment with the revised reference sequences.

8.7 Mutation detection

The UnifiedGenotyper tool in the GATK software was used for mutation detection, and the parameters selected were as follows:

-stand_call_conf 10.0-stand_emit_conf 0-deletions 1.0-glm BOTH-rf BadCigar

In more detail, the parameters used are as the following: set the minimum phred-scaled confidence threshold at which variants should be called to 10.0; the resulting VCF document does not report records with a phred-scaled confidence threshold lower than 0; maximum fraction of reads with deletions spanning this locus for it to be callable; simultaneously detect SNP and Indel; use BadCigar for the automatic filtering of the reads.

8.8 Mutation filtering

The VariantFiltration tool in the GATK software was used to filter the obtained mutation information with the following parameters:

FilterExpression "QD<10.0||ReadPosRankSum<−8.0||FS>10.0||QUAL<$ MEANQUAL*0.5"; the filter name is LowQualFilter; the missing values in expressions should be evaluated as failing; the logging level is set such that only ERROR and FATAL signals are sent to the control screen.

8.9 Mutation statistics:

Mutations in the sequencing data which was matched on the 200 bp at the beginning of the reference sequence and the 200 bp at the end of the reference sequence (pMD18-T vector flanking sequences) was removed, and then statistical analysis was carried out on the sequencing results of each library of each DNA assembly.

9. Sanger sequencing verification:

The DNA assemblies that appear to be completely accurate based on the high-throughput sequencing data were selected, and their corresponding bacterial solutions were used for expansion; then a suitable plasmid extraction kit was used to extract the respective clone plasmids, which were then sent to the sequencing production platform (PGM400) at BGI Shenzhen. In accordance with well-known operating instructions, the Sanger sequencing process was carried out using generic pMD18-T vector primers.

10. Mutation detection by Sanger sequencing

The Sanger sequencing results were aligned with the corresponding reference sequences using BLAST (www.ncbi.nlm.nih.gov/blast), DNAman (www.lynnon.com) and Clustal (www.clustal.org) sequence alignment software, so as to determine whether there is a mutation.

11. Comparing the high-throughput sequencing results and the Sanger sequencing results, the vector DNA samples that showed no mutation in these two approaches were used in subsequent experiments.

The experimental results were analyzed as follows:

Table 1 below lists the number of errors (including single base mutation, nucleotide insertion and deletion, wherein B (i.e., Blank) denotes that the selected clone was a blank vector or a sample with low alignment coverage), as well as the number of errors in the clones with the lowest error number in the 10 libraries. Among a total of 490 clones, 16 clones were selected for Sanger sequencing verification. The consistency of mutation detection was 100%. Among the 49 DNA assemblies, 33 had completely accurate fragments in the 10 selected clones thereof; and 12 clones had the fragments with only one base error. The foregoing results met the expectation.

TABLE 1

Results of the detection on the accuracy rate of 49 successfully assembled DNA assemblies using the high-throughput sequencing strategy

| DNA assembly | Library I | Library II | Library III | Library IV | Library V | Library VI | Library VII | Library VIII | Library IX | Library X | Mix error number |
|---|---|---|---|---|---|---|---|---|---|---|---|
| I1F3SB3P1N11 | B | 1 | B | B | B | 0 | B | B | B | B | 0 |
| I1HoSB11N13 | B | 1 | 0 | B | B | B | 0 | 1 | 0 | B | 0 |
| I1HoSB2P1N14 | B | B | B | B | 0 | 0 | B | 4 | B | 0 | 0 |
| I2F1SB4P1N18 | 3 | 2 | B | 1 | B | B | B | B | 0 | B | 0 |
| I2F1SB6P1N20 | B | B | 1 | B | B | B | 1 | B | B | B | 1 |
| I2RFSB2P1N22 | B | B | B | B | B | B | B | B | B | 1 | 1 |
| I3F1SB2P1N30 | 3 | 0 | B | B | 3 | B | B | B | B | 1 | 0 |
| I3F1SB3P1N31 | B | B | B | 1 | B | B | 3 | B | B | B | 1 |
| I3F1SB4P1N32 | 3 | B | 3 | 4 | B | B | B | B | B | B | 3 |
| I3F2SB1P1N34 | B | B | B | B | B | B | 0 | B | 0 | B | 0 |
| I3F2SB2P1N35 | 1 | 4 | 1 | 0 | 0 | B | 1 | 2 | 3 | B | 0 |
| I3F3SB3P1N40 | B | B | 1 | 2 | 3 | 1 | 0 | 0 | 0 | 2 | 0 |
| I3F3SB4P1N41 | B | B | 2 | 4 | B | 1 | 1 | B | B | 2 | 1 |
| I3F3SB5P1N42 | B | 1 | B | B | B | B | B | B | B | 1 | 1 |
| I3HoSB2P1N44 | B | 3 | B | 1 | 2 | B | B | 0 | 0 | B | 0 |
| I4F1SB2P1N46 | 2 | 0 | 2 | 3 | 0 | B | 3 | 0 | B | 0 | 0 |
| I4F1SB4P1N48 | B | B | 0 | B | B | B | B | B | B | B | 0 |
| I4F2SB1P1N49 | B | B | 0 | 0 | 2 | B | 1 | 0 | B | 2 | 0 |
| I4F2SB2P1N50 | 4 | B | 1 | 6 | B | B | B | 1 | B | 0 | 0 |
| I4F2SB3P1N51 | B | B | 1 | 1 | 4 | B | B | 3 | B | B | 1 |
| I4F2SB4P1N52 | 0 | B | 3 | B | B | B | B | B | B | B | 0 |
| I4F3SB2P1N55 | B | B | B | B | B | B | 0 | 1 | B | 2 | 0 |
| I4F3SB3P1N56 | 3 | B | B | 4 | B | B | B | B | B | B | 3 |
| I4F3SB5P1N58 | 0 | 1 | 1 | 3 | B | 0 | 1 | 2 | 1 | 0 |  |
| I4HoSB1P1N59 | B | 2 | 0 | 1 | B | 0 | 0 | B | 1 | 0 | 0 |
| I4HoSB2P1N60 | B | B | B | B | B | 0 | 2 | B | B | 0 | 0 |
| I5F1SB2P1N62 | 0 | 2 | 0 | 0 | B | 0 | 4 | B | 0 | 2 | 0 |

TABLE 1-continued

Results of the detection on the accuracy rate of 49 successfully assembled DNA assemblies using the high-throughput sequencing strategy

| DNA assembly | Library I | Library II | Library III | Library IV | Library V | Library VI | Library VII | Library VIII | Library IX | Library X | Mix error number |
|---|---|---|---|---|---|---|---|---|---|---|---|
| I5F1SB3P1N63 | 2 | 2 | 6 | 0 | 2 | 4 | 5 | B | B | 2 | 0 |
| I5F1SB4P1N64 | 1 | B | B | 2 | B | 4 | 2 | B | 1 | 0 | 0 |
| I5F2SB1P1N65 | 3 | B | B | 1 | B | B | B | 0 | B | B | 0 |
| I5F2SB2P1N66 | B | B | B | B | B | 0 | B | B | B | B | 0 |
| I5F2SB3P1N67 | B | 1 | B | 2 | B | 2 | 0 | B | 0 | B | 0 |
| I5F3SB1P1N70 | 1 | 1 | B | B | 1 | 2 | 0 | 0 | 3 | B | 0 |
| I5F3SB3P1N72 | B | 2 | 0 | 4 | 1 | 1 | 1 | 2 | B | B | 0 |
| I5F3SB4P1N73 | B | B | B | B | B | 0 | B | B | B | B | 0 |
| I5F3SB5P1N74 | 5 | B | B | B | 3 | B | B | B | B | B | 3 |
| I5HoSB1P1N75 | B | 1 | B | B | B | 2 | 3 | B | B | B | 1 |
| I5HoSB2P1N76 | 2 | B | 2 | B | 1 | B | B | B | 2 | 3 | 1 |
| I6F1SB1P1N77 | 0 | B | 2 | 3 | 2 | 0 | 1 | 1 | 1 | B | 0 |
| I6F1SB2P1N78 | B | B | B | B | B | B | B | 1 | B | B | 1 |
| I6F1SB6P1N82 | 0 | B | B | B | B | B | B | B | B | B | 0 |
| I6F2SB1P1N83 | B | B | 1 | 2 | B | B | B | B | B | B | 1 |
| I6F2SB2P1N84 | B | 0 | B | B | B | B | 3 | 0 | 1 | 1 | 0 |
| I6F2SB4P1N86 | B | B | B | B | B | 2 | 2 | 1 | B | B | 1 |
| I6F2SB5P1N87 | B | 0 | B | B | 1 | B | B | B | 1 | B | 0 |
| I6F2SB6P1N88 | B | B | B | B | B | B | B | 4 | B | 4 | 4 |
| I6HoMSB1P1N89 | 3 | B | 0 | B | 1 | 4 | 2 | B | 0 | 0 | 0 |
| I6HoMSB2P1N90 | 2 | B | 2 | B | 1 | 1 | B | B | B | 3 | 1 |
| I6HoMSB4P1N92 | B | B | 4 | B | 0 | 0 | B | 3 | 3 | 2 | 0 |

The foregoing is a further detailed description of the present invention with the specific embodiments. It should not be determined that the implementation of the present invention is limited to these exemplary embodiments. It will be apparent to one skilled in the art that simple deductions or substitutions can be made without departing from the inventive concept of the present invention.

What is claimed is:

1. A high-throughput detection method for DNA synthesis products, characterized in that the method comprises the following steps:
   1) respectively connecting a plurality of DNA assemblies produced by the synthesis into cloning vectors, which are then respectively transformed into screening bacterial strains, which are respectively cultured on a selection culture medium, so as to enable screening for clones containing the DNA assemblies;
   2) sequentially numbering the clones of each of the DNA assemblies;
   3) selecting the clones assigned the same number but having different DNA assemblies, culturing them in a mixture to obtain a corresponding mixed bacterial solution, and then extracting their plasmids to obtain a mixed plasmid sample; alternatively culturing the clones of each one of the DNA assemblies, respectively, to obtain corresponding bacterial solutions, selecting and mixing the bacterial solutions of the clones assigned the same number but having different DNA assemblies, and extracting their plasmids to obtain a mixed plasmid sample;
   4) attaching sequencing indexes to a plurality of the mixed plasmid samples to construct a plurality of mixed sequencing libraries, wherein the sequencing indexes for different mixed sequencing libraries are different;
   5) carrying out a high-throughput mixed sample sequencing process with the plurality of mixed sequencing libraries, so as to obtain sequences of DNA assemblies carried in selected clones; and
   6) comparing the sequences of the DNA assemblies obtained in the foregoing sequencing process to reference sequences, so as to obtain target DNA assemblies having a preset accuracy rate in the DNA synthesis products.

2. The high-throughput detection method for DNA synthesis products according to claim 1, characterized in that the DNA synthesis products are DNA assemblies synthesized and assembled with a DNA chip.

3. The high-throughput detection method for DNA synthesis products according to claim 1, characterized in that the method further comprises a step between step 1) and step 2): picking selected clones for colony PCR confirmation, so as to further screen for clones having an inserted fragment size consistent with the size of the corresponding DNA assembly.

4. The high-throughput detection method for DNA synthesis products according to claim 1, characterized in that in step 3), the process of mixing clone bacterial solutions is carried out in accordance with the principle of each clone having the same amount of bacteria.

5. The high-throughput detection method for DNA synthesis products according to claim 1, characterized in that step 4) specifically comprises: respectively obtaining or amplifying mixed DNA assemblies from the mixed plasmid samples, and attaching sequencing indexes to a plurality of the mixed DNA assemblies to construct a plurality of mixed sequencing libraries, wherein the sequencing indexes for different mixed sequencing libraries are different.

6. The high-throughput detection method for DNA synthesis products according to claim 5, characterized in that the mixed DNA assemblies are obtained or amplified from the mixed plasmid sample by way of enzymatic digestion or PCR.

7. The high-throughput detection method for DNA synthesis products according to claim 1, characterized in that a sequencing device or a single molecule sequencing device is utilized in the high-throughput sequencing process.

8. The high-throughput detection method for DNA synthesis products according to claim 1, characterized in that the preset accuracy rate refers to base accuracy rate of 100%.

9. The high-throughput detection method for DNA synthesis products according to claim 1, characterized in that the method further comprises: in the case when the preset accuracy rate is lower than 100%, carrying out an error removal process through a single point mutation.

10. The high-throughput detection method for DNA synthesis products according to claim 1, characterized in that the target DNA assemblies are verified by way of a Sanger sequencing process.

11. The high-throughput detection method for DNA synthesis products according to claim 1, characterized in that the method further comprises: in the case when a DNA assembly fails to reach the preset accuracy rate, repeating steps 2) to 6) for the DNA assembly to screen the clones that have not yet been selected, constructing the mixed sequencing libraries and then carrying out sequencing, or repeating steps 4) to 6) for the mixed plasmid samples that have not yet been sequenced, constructing the mixed sequencing libraries and then carrying out sequencing.

12. The high-throughput detection method for DNA synthesis products according to claim 1, characterized in that the method further comprises the following step after step 6): finding a clone and/or a clone bacterial solution corresponding to the target DNA assembly having the preset accuracy rate, and then extracting the plasmid and/or carrying out an amplification process for the DNA assembly.

13. The high-throughput detection method for DNA synthesis products according to claim 4, further comprising preserving the bacterial solution obtained from culturing the clone of each one of the DNA assemblies for future use.

14. The high-throughput detection method for DNA synthesis products according to claim 5, further comprising, after attaching the sequencing indexes, attaching sequencing adaptors to a plurality of the mixed DNA assemblies.

15. The high-throughput detection method for DNA synthesis products according to claim 9, wherein when the preset accuracy rate is lower than 100%, the method further comprises selecting the clones having the lowest single point mutation or mutation of insertion or deletion for the error removal process through the single point mutation.

16. The high-throughput detection method for DNA synthesis products according to claim 9, further comprising confirming a product of the error removal process by way of a Sanger sequencing process.

17. The high-throughput detection method for DNA synthesis products according to claim 15, further comprising confirming a product of the error removal process by way of a Sanger sequencing process.

\* \* \* \* \*